United States Patent [19]

Broka

[11] Patent Number: 5,405,864
[45] Date of Patent: Apr. 11, 1995

[54] CHEMOTHERAPEUTIC MALEIMIDES

[75] Inventor: Chris A. Broka, Foster City, Calif.

[73] Assignee: Syntex (U.S.A.) Inc., Palo Alto, Calif.

[21] Appl. No.: 138,279

[22] Filed: Oct. 15, 1993

[51] Int. Cl.⁶ .................. A61K 31/40; C07D 403/04
[52] U.S. Cl. ........................... 514/415; 514/301;
546/114; 548/464; 548/466
[58] Field of Search ............... 514/301, 415; 548/464,
548/466; 546/114

[56] References Cited

U.S. PATENT DOCUMENTS 5,057,614 10/1991 Davis et al. ..................... 548/466

FOREIGN PATENT DOCUMENTS

| 0328026A1 | 2/1989 | European Pat. Off. ... C07D 403/04 |
| 0384349A1 | 2/1990 | European Pat. Off. ... C07D 403/04 |
| 0397060A2 | 5/1990 | European Pat. Off. ... C07D 403/14 |
| 0470490A1 | 7/1991 | European Pat. Off. ... C07D 471/04 |
| 3914764A1 | 11/1990 | Germany ..................... C07D 403/14 |
| WO91/13071 | 9/1991 | WIPO .......................... C07D 403/14 |
| 9113070 | 9/1991 | WIPO .................................. 548/466 |

OTHER PUBLICATIONS

Toullec, et al., "The Bisindolylmaleimide GF 109203X is a Potent and Selective Inhibitor of Protein Kinase C*", J. Bio. Chem., vol. 266, No. 24, pp. 15771–15781, 1991.

Bit, et al., "Inhibitors of Protein Kinase C. 3. Potent and Highly Selective Bisindolylmaleimides by Conformational Restriction", J. Med. Chem. 1993, 36 21–29.

Davis, et al., "Inhibitors of Protein Kinase C. 1.¹2,3-Bisarylmaleimides", J. Med. Chem. 1992, 35, 177–184.

Davis, et al.,, "A Mild Conversion of Maleic Anhydrides Into Maleimides", Tetrahedron Letters, vol. 31, No. 36, pp. 5201–5204, 1990.

Davis, et al., "A Convenient Synthesis of Bisindolyl- -and Indolylaryl-Maleic Anhydrides", Tetrahedron Letters, vol. 31, No. 16, pp. 2353–2356, 1990.

Davis, et al., "Potent selective inhibitors of protein kinase C", Febs Letters, vol. 259, No. 1, 61–63, Dec. 1989.

Primary Examiner—Mary C. Lee
Assistant Examiner—Jacqueline Haley
Attorney, Agent, or Firm—David A. Lowin; Alan M. Krubiner

[57] ABSTRACT

Maleimide derivatives, i.e., the compounds of Formula I:

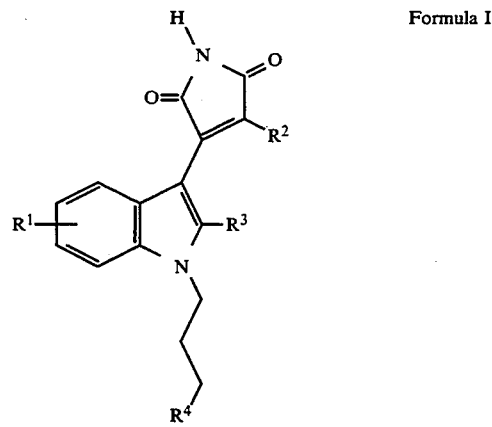

Formula I wherein:
R¹ is H, halo, alkyl, OH, alkoxy, haloalkyl, NO₂, or NR⁵R⁶;
R² is H or CN;
R³ is aryl or heteroaryl, provided that R³ is heteroaryl when R² is H and R⁴ is NR⁵R⁶; and
R⁴ is NR⁵R⁶ or isothiourea,
where R⁵ and R⁶ are independently H or lower alkyl;
and the pharmaceutically acceptable salts thereof, and their use as chemotherapeutic agents.

12 Claims, No Drawings

CHEMOTHERAPEUTIC MALEIMIDES

FIELD OF THE INVENTION

The present invention relates to a series of maleimides. The invention is also directed to formulations and methods for treating malignant diseases.

BACKGROUND INFORMATION

It has long been sought to provide chemotherapeutic agents useful for treating various malignant diseases. The novel maleimides of the present invention are protein kinase C inhibitors useful as chemotherapeutic agents. Other maleimides/substituted pyrroles/protein kinase C inhibitors have been described in the literature as having various activities, such as the treatment of inflammatory, immunological, bronchopulmonary, cadiovascular, malignant, and allergic disorders. See, e.g., U.S. Pat. No. 5,057,614; EPO 0-328-026-A1, 0-384-349-A1; and PCT WO 91/13070 and 91/13071. See also, e.g., the following publications of Davis, et al.: *Febs Letters*, Vol. 259, No. 1, 61-63 (1989); *Tetrahedron Letters*, Vol. 31, No. 16, 2353-2356 (1990); *Tetrahedron Letters*, Vol. 31, No. 36, 5201-5204 (1990); and *J. Med. Chem.*, Vol. 35, 177-184 (1992); and Bit, et al., *J. Med. Chem.*, Vol. 36, 21-29 (1993).

SUMMARY OF THE INVENTION

One aspect of the present invention concerns maleimides, i.e., the compounds of Formula I:

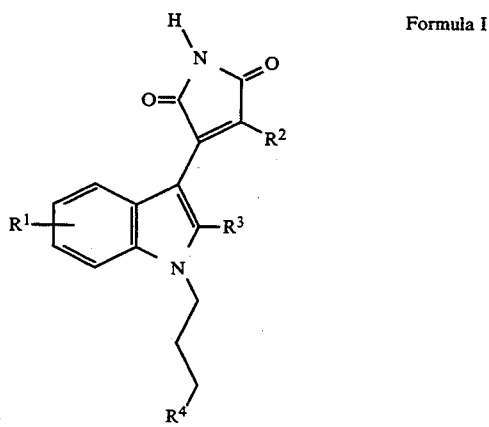

Formula I wherein:
$R^1$ is H, halo, alkyl, OH, alkoxy, haloalkyl, $NO_2$, or $NR^5R^6$;
$R^2$ is H or CN;
$R^3$ is aryl or heteroaryl, provided that $R^3$ is heteroaryl when $R^2$ is H and $R^4$ is $NR^5R^6$; and
$R^4$ is $NR^5R^4$ or isothiourea,
where $R^5$ and $R^6$ are independently H or lower alkyl; and the pharmaceutically acceptable salts thereof.

In a preferred aspect, the invention relates to certain compounds of Formula I, particularly including the compound where $R^1$ is H, $R^2$ is H, $R^3$ is benzothiophene and $R^4$ is $NH_2$, $NHCH_3$ or isothiourea.

In another aspect, the invention relates to a pharmaceutical composition containing a therpeutically effective amount of a compound of Formula I or a pharmaceutically acceptable salt thereof admixed with at least one pharmaceutically acceptable excipient.

In still another aspect, the invention relates to a method of treating malignant disorders, particularly small cell lung carcinoma, colon carcinoma, and tumors corresponding to CHO/PKC-ϵ in a mammal, particularly in a human, by administering to a mammal in need of such treatment a therapeutically effective amount of a compound of Formula I or a pharmaceutically acceptable salt thereof.

In yet another aspect of the invention, the alkylene chain connecting $R^4$ with the indole nitrogen is a group of the formula $(CH_2)_n$ where n is 2-5, preferably 3.

DETAILED DESCRIPTION OF THE INVENTION

Definitions and General Parameters

The following definitions are set forth to illustrate and define the meaning and scope of the various terms used to describe the invention herein.

The term "alkyl" refers to a fully saturated monovalent radical containing only carbon and hydrogen, and which may be a cyclic, branched or straight chain radical. This term is further exemplified by radicals such as methyl, ethyl, t-butyl, pentyl, pivalyl, heptyl and adamantyl.

The term "lower alkyl" refers to a cyclic, branched or straight chain monovalent alkyl radical of one to six carbon atoms. This term is further exemplified by such radicals as methyl, ethyl, n-propyl, isopropyl, n-butyl, t-butyl, i-butyl (or 2-methylpropyl), cyclopropylmethyl, i-amyl. n-amyl, and hexyl.

The term "aryl" refers to a monovalent unsaturated aromatic carbocyclic radical having a single ring (e.g., phenyl), two condensed rings (e.g., naphthyl), or three condensed rings (e.g., phenanthrene) which can optionally be mono-, di- or tri-substituted, independently, with hydroxy, lower alkyl, lower alkoxy, chloro, fluoro, trifluoromethyl, phenyl and/or cyano.

The term "heteroaryl" refers to a monovalent unsaturated aromatic carbocyclic radical having a single ring or two condensed rings, with at least one hetero atom, such as N, O or S, such as quinolyl, benzofuranyl, benzothiophenyl and pyridyl, which can optionally be mono-, di- or tri-substituted, independently, with hydroxy, lower alkyl, lower alkoxy, chloro, fluoro, trifluoromethyl and/or cyano. For purposes of the present invention "heteroaryl" does not include unsubstituted indole.

The term "halo" refers to fluoro, bromo, chloro and iodo.

"Optional" or "optionally" means that the subsequently described event or circumstance may or may not occur, and that the description includes instances where said event or circumstance occurs and instances in which it does not.

A "pharmaceutically acceptable salt" may be any salt derived from an inorganic or organic acid. The term "pharmaceutically acceptable anion" refers to the anion of such acid addition salts. The salt and/or the anion are chosen not to be biologically or otherwise undesirable.

The anions are derived from inorganic acids, such as hydrochloric acid, hydrobromic acid, sulfuric acid (giving the sulfate and bisulfate salts), nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, salicylic acid, p-toluenesulfonic acid and the like.

The term "treatment" or "treating" means any treatment of a disease in a mammal, including:
  (i) preventing the disease, that is, causing the clinical symptoms of the disease not to develop;
  (ii) inhibiting the disease, that is, arresting the development of clinical symptoms; and/or
  (iii) relieving the disease, that is, causing the regression of clinical symptoms.

The term "effective amount" means a dosage sufficient to provide treatment for the disease state being treated. This will vary depending on the patient, the disease and the treatment being effected.

Nomenclature

The compounds of Formula I are named and numbered as described below with reference to Formula II.

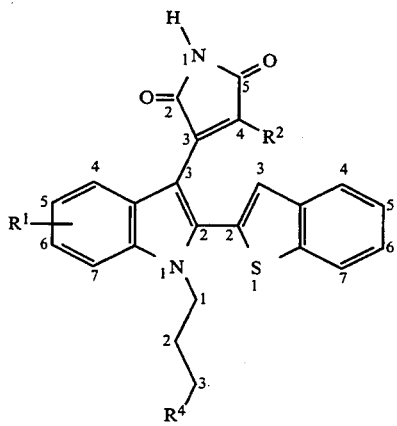

For example, the compound of Formula II where $R^1$ and $R^2$ are hydrogen, and $R^4$ is $NH_2$, a preferred compound of the invention, is named: 3-[1-(3-aminopropyl)-2-(thianaphthen-2-yl)indol-3-yl]-1H-pyrrole-2,5-dione. Alternatively, the compound can be named 3-[1-(3-aminopropyl)-2-(thianaphthen-2-yl)indol-3-yl] maleimide. The thianaphthen-2-yl moiety can also be named benzo[b]thiophen-2-yl under IUPAC nomenclature. While any of these nomenclature systems adequately describes the compounds of the present invention, the former system will be employed for purposes of the present specification. For example, the compounds of Formula I having the following substituents:

| No. | $R^1$ | $R^2$ | $R^3$ | $R^4$ |
|---|---|---|---|---|
| 1 | H | CN | thianaphthen-2-yl | $NH_2$ |
| 2 | H | H | thieno[2,3-b]pyridin-2-yl | isothiourea |
| 3 | H | H | thianaphthen-2-yl | $NHCH_3$ |
| 4 | H | CN | naphthalen-2-yl | $N(CH_3)_2$ |
| 5 | 5-Cl | CN | thianaphthen-2-yl | isothiourea |
| 6 | 7-$NO_2$ | H | phenanthren-2-yl | $NHCH_3$ | are respectively named as follows:
1. 3-[1-(3-aminopropyl)-2-(thianaphthen-2-yl)indol-3-yl]-4-cyano-1H-pyrrole-2,5-dione;
2. 3-[1-(3-isothioureidopropyl)-2-(thieno[2,3-b]pyridin-2-yl)indol-3-yl]-1H-pyrrole-2,5-dione;
3. 3-[1-(3-N-methylaminopropyl)-2-(thianaphthen-2-yl)indol-3-yl]-1H-pyrrole-2,5-dione;
4. 4-cyano-3-[1-(3-N,N-dimethylaminopropyl)-2-(thianaphthen-2-yl)indol-3-yl]-1H-pyrrole-2,5-dione;
5. 4-cyano-3-[5-chloro-1-(3-isothioureidopropyl)-2-(thianaphthen-2-yl)indol-3-yl]-1H-pyrrole-2,5-dione;
6. 3-[1-(3-N-methylaminopropyl)-7-nitro-2-(phenanthren-2-yl)indol-3-yl]-1H-pyrrole-2,5-dione;

Synthetic Reaction Parameters

The terms "solvent", "inert organic solvent" or "inert solvent" mean a solvent inert under the conditions of the reaction being described in conjunction therewith [including, for example, benzene, toluene, acetonitrile, tetrahydrofuran ("THF"), dimethylformamide ("DMF"), chloroform, methylene chloride (or dichloromethane), diethyl ether, methanol, pyridine and the like]. Unless specified to the contrary, the solvents used in the reactions of the present invention are inert organic solvents.

The term "q.s." means adding a quantity sufficient to achieve a stated function, e.g., to bring a solution to the desired volume (i.e., 100%).

Unless specified to the contrary, the reactions described herein take place at atmospheric pressure within a temperature range from 5° C. to 100° C. (preferably from 10°°C. to 50° C.; most preferably at "room" or "ambient" temperature, e.g., 20° C.). Further, unless otherwise specified, the reaction times and conditions are intended to be approximate, e.g., taking place at about atmospheric pressure within a temperature range of about 5° C. to about 100° C. (preferably from about 10° C. to about 50° C.; most preferably about 20° C.) over a period of about 1 to about 10 hours (preferably about 5 hours). Parameters given in the Examples are intended to be specific, not approximate.

Isolation and purification of the compounds and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples hereinbelow. However, other equivalent separation or isolation procedures can, of course, also be used.

Synthesis of the Compounds of Formula I

The compounds of Formula I can be prepared by following the procedures described below with reference to Reaction Schemes 1 and 2. As used in the Reaction Schemes, the substituents, e.g., $R^1$, $R^2$, and $R^3$ have the same meaning as described in the Summary of the Invention. The substituent $OSiPh_2$-t-Bu refers to t-butyl-diphenylsilyloxy.

Starting Materials

The compound thianaphthene (also named benzothiophene) is commercially available, e.g., from Aldrich Chemical Company, Milwaukee, Wis. Other reactants, such as the aryl methyl ketones and 1-iodo-3-(t-butyl)-diphenyl-silyloxypropane are likewise commercially available or may be readily prepared by those skilled in the art using commonly employed synthetic methodology.

Reaction Scheme A

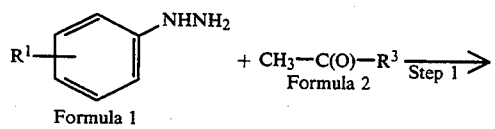

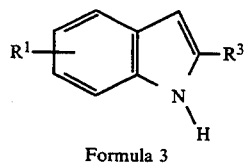

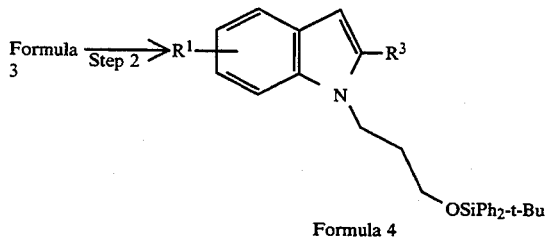

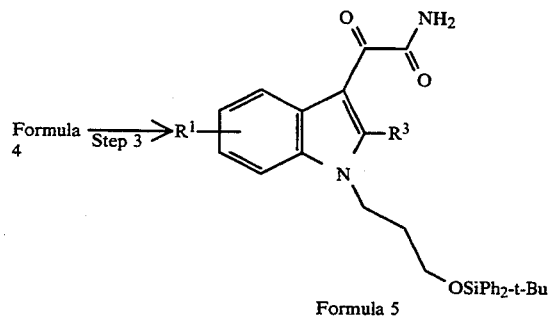

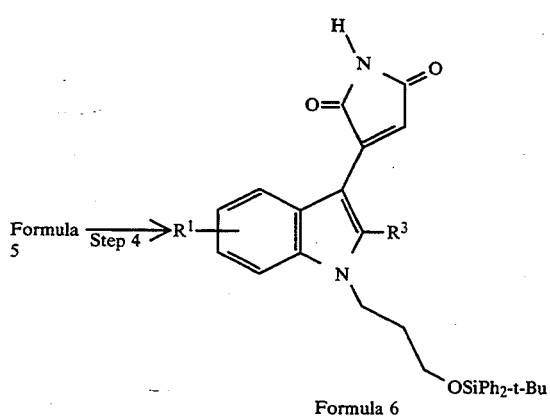

-continued
Reaction Scheme A

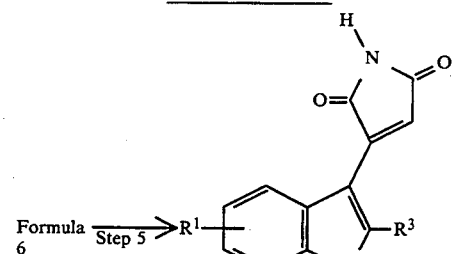

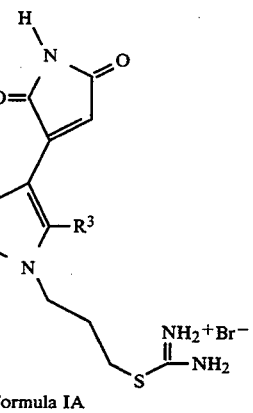

Preparation of Formula 3

As illustrated in Reaction Scheme A, Step 1, an appropriately substituted phenylhydrazine of Formula 1 and an appropriate aryl or heteroaryl methyl ketone of Formula 2 are dissolved in a lower alkanol solvent (EToH is preferred but MeOH or i-PrOH can be employed), refluxed for 1-12 hours, and allowed to cool to room temperature. Upon cooling, a precipitation of crystals (a hydrazone) are filtered off and dried. The hydrazone obtained is dissolved An 85% $H_3PO_4$ or mixed with $ZnCl_2$ then heated at 150°14 220° C. for 15 minutes to 3 hours. After cooling, the reaction mixture is digested with $CH_2Cl_2$ and $H_2O$. The $CH_2Cl_2$ layer is evaporated and the corresponding (optionally substituted) 2-(aryl or heteroaryl) indole of Formula 3 is purified either by recrystallization or silica gel chromatography.

Preparation of Formula 4

As illustrated in Reaction Scheme A, Step 2, an (optionally substituted) 2-(aryl or heteroaryl) indole of Formula 3 is dissolved in DMF (or DMSO, THF, or DME) and treated with KH or NaH. After stirring for 30 minutes to 2 hours, a halogenated protecting compound (such as bromo-(t-butyl)dimethylsilyloxypropane or 1-iodo-3-(t-butyl)diphenylsilyloxypropane, the latter being shown in the reaction schemes for purposes of illustration) is added. After 1-12 hours, the mixture Is partitioned between $Et_2O$ and $H_2O$. The product, a 2-(aryl or heteroaryl)-N-[3-(t-butyl)diphenylsilyloxypropyl] indole of Formula 4 is purified either by crystallization or silica gel chromatography.

Preparation of Formula 5

As illustrated in Reaction Scheme A, Step 3, a solution of a 2-(aryl or heteroaryl)-N-[3-(t-butyl)diphenylsilyloxypropyl] indole of Formula 4 in $CH_2Cl_2$ or $Et_2O$ is treated with $(COCl)_2$ at 0°–20° C. for 30 minutes to 1 hour. The resulting solution is poured into cold conc. $NH_4OH$. After several minutes, the mixture is filtered and the filtrate is washed with $CH_2Cl_2$. The $CH_2Cl_2$ extracts are evaporated and the corresponding glyoxylamide of Formula 5 is purified by silica gel chromatography.

Preparation of Formula 6

As illustrated in Reaction Scheme A, Step 4, a solution of the potassium salt of trimethyl phosphonoacetate is prepared in a polar solvent such as MeOH, DMF, or THF using KH or KHMPS as the base. A glyoxylamide of Formula 5 is added to this solution at 0°–20° C. and stirred for 1–24 hours. The mixture was partitioned between EtOAc and $NaHCO_3$ (aq.) and the corresponding maleimide of Formula 6 is purified by silica gel chromatography.

Preparation of Formula 7

As illustrated in Reaction Scheme A, Step 5, the silyl group of a maleimide of Formula 6 is removed by treatment with a tetraalkylammonium fluoride in a solvent (preferably THF) at 0°–30° C. for 1–12 hours. The resulting alcohol (not shown) is purified by silica gel chromatography, then converted into the corresponding bromide.

Conversion of the alcohol into the bromide is accomplished by dissolving the alcohol in a solvent (preferably $CH_2Cl_2$ or THF) and treating it first with a triarylphosphine and then with NBS. After 15 minutes to 4 hours at 20°–30° C., the reaction mixture is partitioned between EtOAc or $CH_2Cl_2$ and aq. $NaHCO_3$. The corresponding 4-bromopropyl maleimide of Formula 7 is purified by silica gel chromatography.

Preparation of Formula IA

As illustrated in Reaction Scheme A, Step 6, a bromide of Formula 7 is dissolved in ETOH (preferred), MeOH, PrOH, or i-PrOH (with THF added optionally). Thiourea is added and the reaction allowed to reflux for 12–48 hours. After removal of the solvent, the corresponding (optionally substituted) 2-(aryl or heteroaryl)-N-(4-thiourea)propyl-indol-3-yl maleimide of Formula IA is purified by chromatography on silica gel or crystallization.

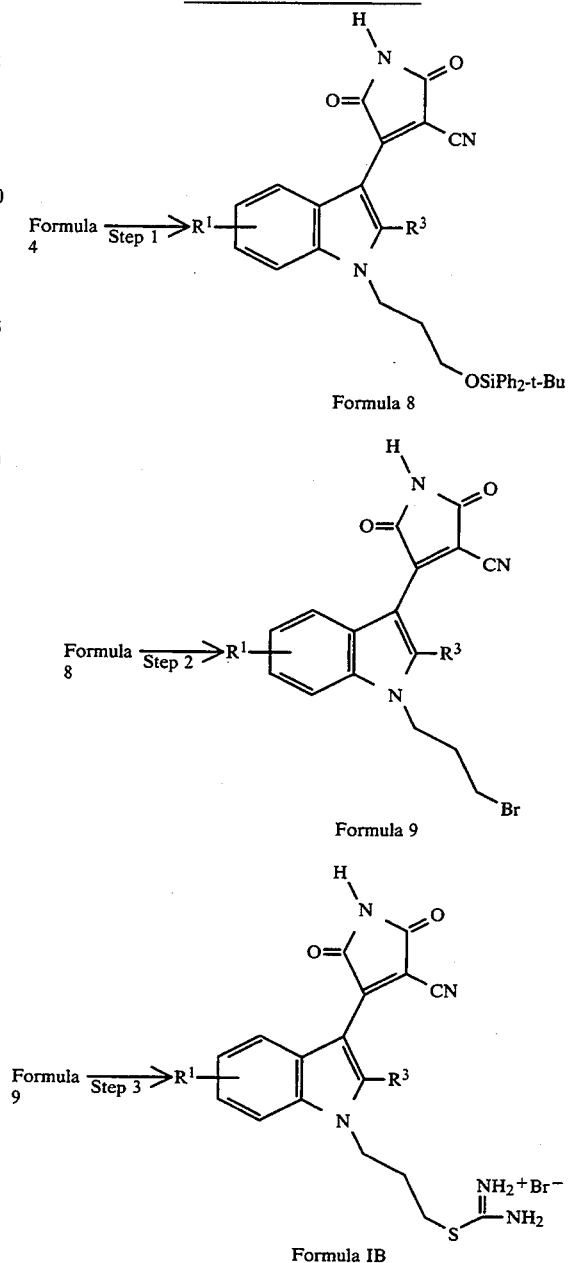

REACTION SCHEME B

Formula 4 —Step 1→ $R^1$ Formula 8

Formula 8 —Step 2→ $R^1$ Formula 9

Formula 9 —Step 3→ $R^1$ Formula IB

Preparation of Formula 8

As illustrated in Reaction Scheme B, Step 1, a solution of an (optionally substituted) 2-(aryl or heteroaryl) indole of Formula 4 in a solvent such as THF or $Et_2O$ is treated with 3-chloro-4-cyanomaleimide [Wiley, R. H.; Slaymaker, S. C. JACS, 80, 1385 (1958)]. After stirring at 0°–35° C. for 30 minutes to 12 hours, the mixture is partitioned between $Et_2O$ and aq. $NaHCO_3$. The corresponding maleimide of Formula 8 is purified by silica gel chromatography.

Preparation of Formula IB

As illustrated in Reaction Scheme B, Steps 2 and 3, a maleimide of Formula 8 is converted via the corresponding bromide of Formula 9 to the corresponding (optionally substituted) 2-(aryl or heteroaryl)-N-(4-thiourea)propyl-indol-3-yl cyanomaleimide of Formula IB by following the procedures described above with respect to Reaction Scheme A, Steps 5 and 6.

REACTION SCHEME C

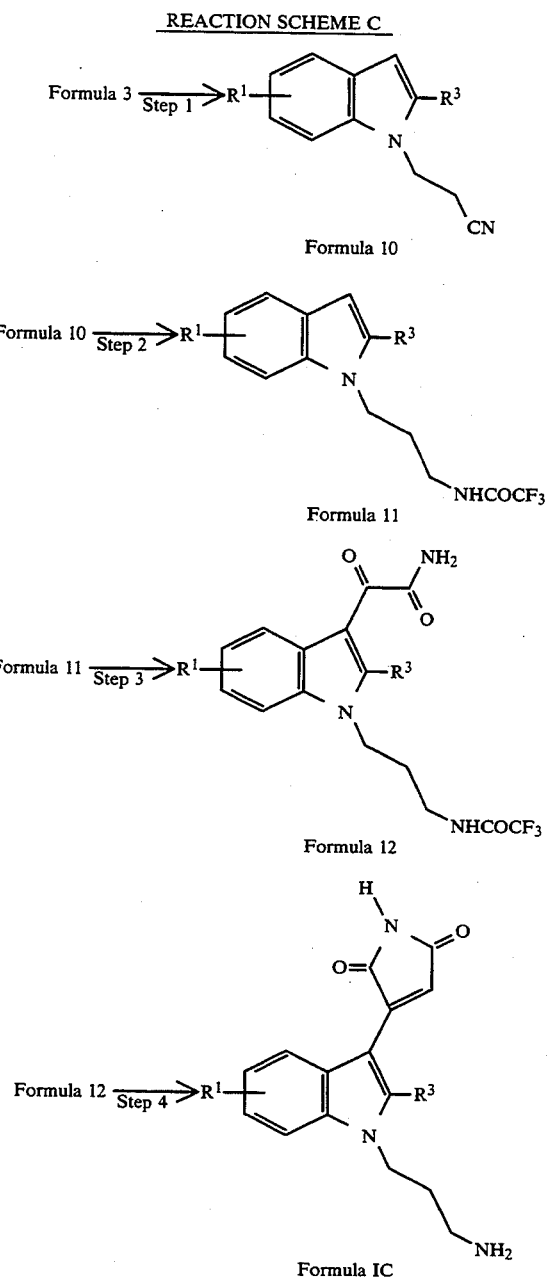

Formula 10

Formula 11

Formula 12

Formula IC

Preparation of Formula 10

As illustrated in Reaction Scheme C, Step 1, an optionally substituted indole of Formula 3 is stirred with acrylonitrile and a base (preferrably NaOH) in a hydrocarbon solvent (e.g., benzene, toluene) containing a phase-transfer catalyst. After consumption of the starting indole (determined by TLC), the mixture is diluted with EtOAc and filtered. The solvent is removed under vacuum and the corresponding nitrile of Formula 10 is used directly, without further purification.

Preparation of Formula 11

As illustrated in Reaction Scheme C, Step 2, a nitrile of Formula 10 is dissolved in an etherial solvent (THF preferred) and reduced to the corresponding amine (not shown) using $BH_3$ (LAH, Red-Al may also be used) at 20°–65° C. for 1–12 hours. The reaction mixture is partitioned between EtOAc and $H_{2O}$ and the amine is purified by silica gel chromatography.

The amine is then taken up in $CH_2Cl_2$ or another non-protic solvent and treated with pyridine and $(TFA)_2O$ for 15 minutes to 1 hour at 0°–25° C. After partitioning the reaction mixture between EtOAc and aq. $NaHCO_3$, the corresponding trifluoroacetamide of Formula 11 is purified by silica gel chromatography.

Preparation of Formula IC

As illustrated in Reaction Scheme C, Steps 3 and 4, a trifluoroacetamide of Formula 11 is converted via the glyoxylamide of Formula 12 to the corresponding (optionally substituted) 2-(aryl or heteroaryl)-N-4-aminopropyl-indol-3-yl maleimide of Formula IC by following the procedures described above with respect to Reaction Scheme A, Steps 3 and 4.

REACTION SCHEME D

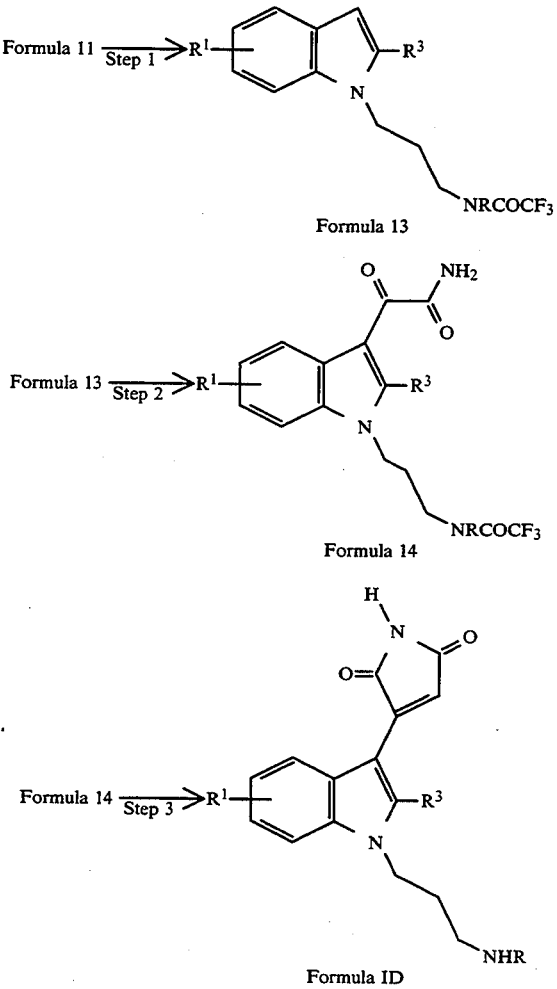

Formula 13

Formula 14

Formula ID

Preparation of Formula 13

As illustrated in Reaction Scheme D, Step 1, a trifluoroacetamide of Formula 11 in solution with THF is treated with KH until $H_2$ evolution ceases. A catalytic amount of 18-crown-6 is introduced followed by an alkyl halide, rosylate or mesylate. After 1–12 hours at 0°–25° C., the mixture is partitioned between EtOAc and H₂O. The corresponding lower alkyl-trifluoroacetamide of Formula 13 is purified by silica gel chromatography.

Preparation of Formula ID

As illustrated in Reaction Scheme D, Steps 2 and 3, a lower alkyltrifluoroacetamide of Formula 13 is converted via the glyoxylamide of Formula 14 to the corresponding (optionally substituted) 2-(aryl or heteroaryl)-N-4-(lower alkyl)aminopropyl-indol-3-yl maleimide of Formula ID (i.e., a compound of Formula I where $R^4$ is $NR^5R^6$ and one of $R^5$ and $R^6$ is H while the other, shown as "R" in the reaction scheme, is lower alkyl) by following the procedures described above with respect to Reaction Scheme A, Steps 3 and 4.

REACTION SCHEME E

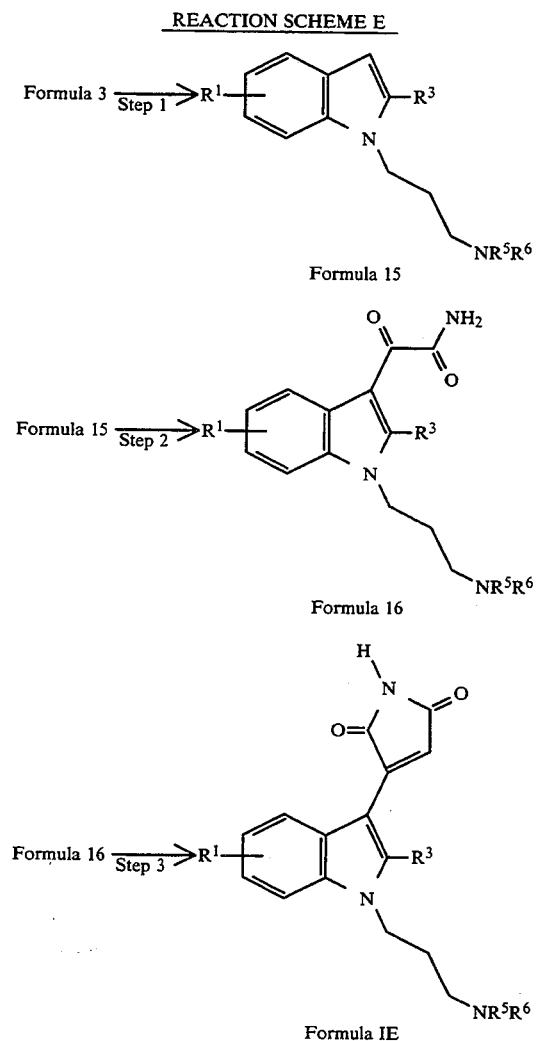

Preparation of Formula 15

As illustrated in Reaction Scheme E, Step 1, an indole of Formula 3 is treated with KH or NaH until H₂ evolution ceases. A 1-halo-3-dialkylaminopropane is then added and the reaction allowed to proceed for 1 to 12 hours at 0° to 25° C. The mixture is then partitioned between Et₂O and H₂O. The corresponding dialkylaminopropylindole of Formula 15 (where $R^5$ and $R^6$ are both lower alkyl) is purified by silica gel chromatography.

Preparation of Formula IE

As illustrated in Reaction Scheme E, Steps 2 and 3, a dialkylaminopropylindole of Formula 15 is converted via the glyoxylamide of Formula 16 to the corresponding (optionally substituted) 2-(aryl or heteroaryl)-N-4-(di-lower alkyl)aminopropyl-indol-3-yl maleimide of Formula IE by following the procedures described above with respect to Reaction Scheme A, Steps 3 and 4.

Preparation of the Salts of Formula I

Some of the compounds of Formula I can be converted to corresponding acid addition salts. The conversion is accomplished by treatment with a stochiometric amount of an appropriate acid, such as hydrochloric acid (e.g., 3 molar equivalents to form the trihydrochloride salt). Typically, the free base is dissolved in a polar organic solvent, such as methanol or ethanol, and the acid is added in water, methanol or ethanol. The temperature is maintained at 0° C. to 50° C. The corresponding salt precipitates spontaneously or can be brought out of solution with a less polar solvent.

The acid addition salts of the compounds of Formula I can be decomposed to the corresponding free bases by treatment with an excess of a suitable base, such as ammonia or sodium bicarbonate, typically in the presence of an aqueous solvent, and at a temperature between 0° C. and 50° C. The free base form is isolated by conventional means, such as extraction with an organic solvent.

PREFERRED COMPOUNDS

Preferred are the compounds of Formula I where $R^1$ and $R^2$ are H. Also preferred are those compounds where $R^3$ is thianaphthen-2-yl. Also preferred are those compounds where $R^4$ is $NH_2$, $NHCH_3$ or isothiourea. Further preferred are those compounds which combine the above-mentioned features. Most preferred are the compounds:

3-[1-(3-isothioureidopropyl)-2-(thianaphthen-2-yl)indol-3-yl]-1H-pyrrole-2,5-dione; and 3-[1-(3-aminopropyl)-2-(thianaphthen-2-yl)indol-3-yl]-1H-pyrrole-2,5-dione.

UTILITY, TESTING, AND ADMINISTRATION

General Utility

The compounds of the present invention are protein kinase C inhibitors useful as chemotherapeutic agents for treating mammals, particularly humans, having a variety of malignant disease states including: small cell lung carcinoma, colon carcinoma, breast tumors corresonding to MCF7, MDA-MB-435 and MDA-N cell lines, and PKC overexpressing tumors, such as those corresponding to CHO/PKC-ε. Different compounds of the invention exhibit greater activity against certain tumors as opposed to others, as can be determined by commonly used methods. For example, 3-[1-(3-isothioureidopropyl)-2-(thianaphthen-2-yl)indol-3-yl]-1H-pyrrole-2,5-dione has a GI₅₀ (concentration to inhibit tumor cell growth in culture by 50%) of 10 nN against breast cell line MDA-N versus 1 μM against colon carcinoma cell line HT-29.

Testing

In vitro activity for protein kinase C inhibition, is quantitated by measuring incorporation of $^{32}P$ from $\gamma$-$^{32}P$ ATP into synthetic peptide substrates.

In vivo activity for chemotherapeutic agents, particularly for treating malignant diseases, is determined by tumor inhibition assays, for example as described by Maneckjee, et al., in *Proc. Natl. Acad. Sci. USA*, Vol 89, 1169–1173 (February 1992). Variations of the assay can be performed, e.g., using HT-29 colon carcinoma cells, SCLC $H_{82}$ cells, CHO/PKC-$\beta$ and CHO/PKC-$\epsilon$ cells.

Administration

The compounds of Formula I are administered at a therapeutically effective dosage, e.g., a dosage sufficient to provide treatment for the disease states previously described. Administration of the compounds of the invention or the pharmaceutically acceptable salts thereof can be via any of the accepted modes of administration for agents that serve similar utilities.

While human dosage levels have yet to be optimized for the compounds of the invention, generally, a daily dose is from about 0.1 to 20.0 mg/kg of body weight, preferably about 0.5 to 10.0 mg/kg of body weight, and most preferably about 1.0 to 5.0 mg/kg of body weight. Thus, for administration to a 70 kg person, the dosage range would be about 7.0 to 1,400 mg per day, preferably about 35.0 to 700 mg per day, and most preferably about 70 to 350 mg per day. The amount of active compound administered will, of course, be dependent on the subject and disease state being treated, the severity of the affliction, the manner and schedule of administration and the judgment of the prescribing physician.

In employing the compounds of this invention for treatment of the above conditions, any pharmaceutically acceptable mode of administration can be used. The compounds of Formula I can be administered either alone or in combination with other pharmaceutically acceptable excipients, including solid, semi-solid, liquid or aerosol dosage forms, such as, for example, tablets, capsules, powders, liquids, suspensions, suppositories, aerosols or the like. The compounds of Formula I can also be administered in sustained or controlled release dosage forms, including depot injections, osmotic pumps, pills, transdermal (including electrotransport) patches, and the like, for the prolonged administration of the compound at a predetermined rate, preferably in unit dosage forms suitable for single administration of precise dosages. The compositions will typically include a conventional pharmaceutical carrier or excipient and a compound of Formula I or a pharmaceutically acceptable salt thereof. In addition, these compositions may include other medicinal agents, pharmaceutical agents, carriers, adjuvants, etc., such as multidrug resistance reversing agents.

Generally, depending on the intended mode of administration, the pharmaceutically acceptable composition will contain about 0.1% to 90%, preferably about 0.5% to 50%, by weight of a compound or salt of Formula I, the remainder being suitable pharmaceutical excipients, carriers, etc.

One preferred manner of administration for the conditions detailed above is oral, using a convenient daily dosage regimen which can be adjusted according to the degree of affliction. For such oral administration, a pharmaceutically acceptable, non-toxic composition is formed by the incorporation of any of the normally employed excipients, such as, for example, mannitol, lactose, starch, magnesium stearate, sodium saccharine, talcum, cellulose, sodium crosscarmellose, glucose, gelatin, sucrose, magnesium carbonate, and the like. Such compositions take the form of solutions, suspensions, tablets, dispersible tablets, pills, capsules, powders, sustained release formulations and the like.

Preferably the compositions will take the form of a pill or tablet and thus the composition will contain, along with the active ingredient, a diluent such as lactose, sucrose, dicalcium phosphate, or the like; a lubricant such as magnesium stearate or the like; and a binder such as starch, gum acacia, polyvinylpyrrolidine, gelatin, cellulose and derivatives thereof, and the like.

Liquid pharmaceutically administrable compositions can, for example, be prepared by dissolving, dispersing, etc. an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, sodium acetate, sodium citrate, cyclodextrine derivatives, sorbitan monolaurate, triethanolamine acetate, triethanolamine oleate, etc. Actual methods of preparing such dosage forms are known, or will be apparent, to those skilled in this art; for example, see *Remington's Pharmaceutical Sciences*, Mack Publishing Company, Easton, Pa., 15th Edition, 1975. The composition or formulation to be administered will, in any event, contain a quantity of the active compound in an amount effective to alleviate the symptoms of the subject being treated.

Dosage forms or compositions containing active ingredient in the range of 0.005% to 95% with the balance made up from non-toxic carrier may be prepared.

For oral administration, a pharmaceutically acceptable non-toxic composition is formed by the incorporation of any of the normally employed excipients, such as, for example pharmaceutical grades of mannitol, lactose, starch, magnesium stearate, talcum, cellulose derivatives, sodium crosscarmellose, glucose, sucrose, magnesium carbonate, sodium saccharin, talcum and the like. Such compositions take the form of solutions, suspensions, tablets, capsules, powders, sustained release formulations and the like. Such compositions may contain 0.01%–95% active ingredient, preferably 0.1–50%.

For a solid dosage form, the solution or suspension, in for example propylene carbonate, vegetable oils or triglycerides, is preferably encapsulated in a gelatin capsule. Such diester solutions, and the preparation and encapsulation thereof, are disclosed in U.S. Pat. Nos. 4,328,245; 4,409,239; and 4,410,545. For a liquid dosage form, the solution, e.g. in a polyethylene glycol, may be diluted with a sufficient quantity of a pharmaceutically acceptable liquid carrier, e.g. water, to be easily measured for administration.

Alternatively, liquid or semi-solid oral formulations may be prepared by dissolving or dispersing the active compound or salt in vegetable oils, glycols, triglycerides, propylene glycol esters (e.g. propylene carbonate) and the like, and encapsulating these solutions or suspensions in hard or soft gelatin capsule shells.

Other useful formulations include those set forth in U.S. Pat. Nos. Re. 28,819 and 4,358,603.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents, solubility enhancers, and the like, such as for example, sodium acetate, sorbitan monolaurate, triethanolamine oleate, cyclodextrins, etc. A more recently devised approach for parenteral administration employs the implantation of a slow-release or sustained-release system, such that a constant level of dosage is maintained. See, e.g., U.S. Pat. No. 3,710,795.

The percentage of active compound contained in such parenteral compositions is highly dependent on the specific nature thereof, as well as the activity of the compound and the needs of the subject. However, percentages of active ingredient of 0.01% to 10% in solution are employable, and will be higher if the composition is a solid which will be subsequently diluted to the above percentages. Preferably the composition will comprise 0.2–2% of the active agent in solution.

Nasal solutions of the active compound alone or in combination with other pharmaceutically acceptable excipients can also be administered.

Formulations of the active compound or a salt may also be administered to the respiratory tract as an aerosol or solution for a nebulizer, or as a microfine powder for insufflation, alone or in combination with an inert carrier such as lactose. In such a case, the particles of the formulation have diameters of less than 50 microns, preferably less than 10 microns.

EXAMPLES

The following preparations and examples are given to enable those skilled in the art to more clearly understand and to practice the present invention. They should not be considered as limiting the scope of the invention, but merely as being illustrative and representative thereof.

EXAMPLE 1

1A. Formula 3 Where $R^1$ is H and $R^3$ is Thianaphthen-2-yl

To a 0° C. solution of thianaphthene (23.9 g, 178 mmol) in 200 mL of 1:1 THF/Et$_2$O was added 134 mL of n-butyl lithium in hexane (1.6M, 214 mmol) at a rate such that the internal reaction temperature remained below 4° C. Following this addition, the cooling bath was removed and the resulting heterogeneous mixture was stirred for 1 hour at room temperature and then cooled to 0° C. A solution of acetaldehyde (19.6 g, 445 mmol) in 25 mL of THF was quickly added. The ice bath was removed and after 10 min. the reaction was quenched by the addition of 800 mL of water. The layers were separated and the aqueous layer was extracted with 3×200 mL of Et$_2$O. The combined organic extracts were washed with brine, dried over MgSO$_4$, and concentrated to yield an amber oil that was purified by silica gel chromatography (7–15% EtOAc/hexane) to yield 14.6 g (46%) of 2-(1-hydroxyethyl)thianaphthene as a pale yellow oil: $^1$H NMR (300 MHz, CDCl$_3$) δ1.62 (d, J=6.7 Hz, 3H), 5.17 (q, J=6.6 Hz, 1H), 7.16 (s, 1H), 7.2–7.35 (m, 2H), 7.7 (m, 1H), 7.8 (m, 1H).

A solution of the above alcohol in 400 mL of CH$_2$Cl$_2$ was treated with pyridinium chlorochromate ("PCC") (17.5 g, 1 eq) along with 18 g of celite. After one hour, additional PCC was added (17.5 g) along with 18 g of celite. The reaction was followed by TLC and filtered through a bed of silica gel when starting material was no longer detected. The remaining solid was washed with several portions of CH$_2$Cl$_2$. Evaporation gave 13.3 g (93%) of crystalline 2-(1-oxoethyl)thianaphthene: $^1$H NMR (300 MHz, CDCl$_3$) δ2.67 (s, 3H), 7.35–7.5 (m, 2H), 7.85–7.9 (m, 2H), 7.91 (s,1H).

A solution of the above ketone (13.3 g, 75 mmol) in 65 mL of absolute EtOH was treated with phenylhydrazine (9.78 g, 90.5 mmol) and heated to reflux for 1.75 hours. The dark yellow solution was cooled to room temperature and then placed in a −20° C. freezer for several hours. The resulting yellow solid hydrazone was collected (13.9 g) and the filtrate was concentrated and dissolved in hot EtOH. Upon cooling, an addition 3.8 g of yellow solid was obtained. The combined hydrazone samples were treated with 85 mL of 85% H$_3$PO$_4$ and placed in a 180° C. oil bath for 40 min. The resulting brown, hetero-geneous mixture was cooled to 100° C. and 75 mL of water was cautiously added. The mixture was transferred to a larger flask and an additional 150 mL of water was added and the mixture was heated to reflux for 1 hour and then cooled to room temperature. Filtration gave 11.3 g of brown solid, which was purified by partially dissolving in 75 mL of hot EtOH. Filtration of this mixture gave 7.1 g (54%) of 2-(thianaphthen-2-yl)indole as a brown powder: $^1$H NMR (300 MHz, acetone) δ6.87 (s, 1H), 7.07 (t, J=7.4 Hz, 1H), 7.18 (t, J=7.1 Hz, 1H), 7.38 (m, 2H), 7.45 (d, J=8.1 Hz, 1H), 7.60 (d, J=7.8 Hz, 1H), 7.77 (s, 1H), 7.83 (m, 1H), 7.93 (m, 1H); $^{13}$C NMR (75.4 MHz, acetone) δ102.16, 112.01, 112.06, 119.89, 120.86, 121.33, 123.05, 123.52, 124.39, 125.46, 125.65, 129.84, 136.7, 138.5, 139.78, 141.5.

1B. Formula 3, Varying $R^1$ and $R^3$

By following the procedure of part A and substituting thianaphthene, e.g., with other heteroaryl or aryl groups corresponding to the desired $R^3$ substituent, and/or substituting phenylhydrazine other compounds of Formula 1 corresponding to the desired $R^1$ substituent, there are obtained the corresponding compounds of Formula 3 as identified in the following table.

| | Formula 3 |
|---|---|
| $R^1$ | $R^3$ |
| H | Phenyl |
| H | 4-Methylphenyl |
| H | Biphenyl-4-yl |
| H | Naphthalen-1-yl |
| H | Naphthalen-2-yl |
| H | 6-Methoxy-naphthalen-2-yl |
| H | 5,7-Dihydroxy-naphth-1-yl |
| H | 5,5,8,8-tetramethyl-5,5,8,8-tetrahydro-naphthalen-2-yl |
| H | Phenanthren-2-yl |
| H | Phenanthren-3-yl |
| H | 9H-Fluoren-2-yl |
| H | Thien-3-yl |
| H | Thieno[2,3-b]-pyridin-2-yl |
| H | 2,3-Dihydro-benzo[1,4]dioxin-6-yl |

| Formula 3 | |
|---|---|
| R[1] | R[3] |
| H | 2-Cyanoindol-3-yl |
| H | Naphtho[2,1-b]-thiophen-2-yl |
| H | Naphtho[1,2-b]-thiophen-2-yl |
| H | Benzofuran-2-yl |
| 5-Fluoro | Benzo[b]-thiophen-2-yl |
| 5-Chloro | Benzo[b]-thiophen-2-yl |
| 4-Methyl | Biphenyl-4-yl |
| 6-t-Butyl | Naphthalen-2-yl |
| 7-Hydroxy | Phenanthren-2-yl |
| 6-Trifluoromethyl | Thieno[2,3-b]-pyridin-2-yl |
| 7-Nitro | Naphtho[2,1-b]-thiophen-2-yl |
| 5-Amino | Benzofuran-2-yl |
| 6-Dimethylamino | Benzo[b]-thiophen-2-yl |

EXAMPLE 2

2A. Formula 4 Where R[1] is H and R[3] is Thianaphthen-2-yl 2-(Thianaphthen-2-yl)indole (2.5 g) was added, in 10 ml DMF, to 500 mg KH in 5 ml DMF and the mixture was stirred at 20° C. for 30 minutes under $N_2$. 1-Iodo-3-t-butyldiphenylsilyloxypropane (5 g) was then introduced via syringe. After stirring 1 hour, the mixture was poured into $H_2O$ and extracted with $Et_2O$. The $Et_2O$ extract was dried ($K_2CO_3$) and concentrated to an oil. MeOH (~20 ml) was added and crystallization induced by scratching. The product, 1-(3-t-butyldiphenylsilyloxypropyl)-2-(thianaphthen-2-yl)indole a yellowish powder, was collected by filtration.

Yield 4.5 g, m.p. 101°-103° C.

2B. Formula 4, Varying R[1] and R[3]

By following the procedure of Part A and substituting 2-(thianaphthen-2-yl)indole with the compounds of Formula 3, e.g., as prepared in Example 1B above, there are obtained the corresponding compounds of Formula 4.

EXAMPLE 3

3A. Formula 5 Where R[1] is H and R[3] is Thianaphthen-2-yl

A solution of 1-(3-t-butyldiphenylsilyloxypropyl)-2-(thianaphthen-2-yl)indole (2.3 g) in 20 ml $CH_2Cl_2$ was treated with 500 μl oxalyl chloride and stirred for 30 minutes. The resulting solution was then poured into 60 ml of cold, rapidly stirred, conc. $NH_4OH$. The mixture was filtered through Celite and the precipitate washed with $CH_2Cl_2$. The $CH_2Cl_2$ layer from the filtrate was collected and the aqueous layer washed with additional $CH_2Cl_2$. (The solid precipitate was discarded). The combined $CH_2Cl_2$ layers were dried over $K_2CO_3$ and evaporated. The product, 1-(3-t-butyldiphenylsilyloxypropyl)-2-(thianaphthen-2-yl)indol-3-yl glyoxylamide was purified by flash chromatography over silica gel (EtOAc/hexane).

3B. Formula 5, Varying R[1] and R[3]

By following the procedure of Part A and substituting 1-(3-t-butyldiphenylsilyloxypropyl)-2-(thianaphthen-2-yl)indole with the compounds of Formula 4, e.g., as prepared in Example 2B above, there are obtained the corresponding glyoxylamide compounds of Formula 5.

EXAMPLE 4

A. Formula 6 Where R[1] and R[2] are B and R[3] is Thianaphthen-2-yl

Trimethyl phosphonoacetate (640 μl) was added dropwise to a suspension of 160 mg KH in 10 ml DMF. After formation of the anion was complete (15 min.), a solution of 1-(3-t-butyldiphenyl-silyloxypropyl)-2-(thianaphthen-2-yl)indol-3-yl glyoxylamide (300 mg) in 3 ml DMF was added. After stirring 6 h at 20° C., the mixture was partitioned between EtOAc and $H_2O$ and the product from the organic layer was purified by preparative TLC (2.5:1 hexane/EtOAc). The maleimide product, 3-[1-(3-t-butyldiphenylsilyloxypropyl)-2-(thianaphthen-2-yl)indol-3-yl]-1H-pyrrole-2,5-dione was obtained as a bright yellow foam (110 mg, 35%).

4B. Formula 6, Varying R[1] and R[3]

By following the procedure of Part A and substituting 1-(3-t-butyldiphenylsilyloxypropyl)-2-(thianaphthen-2-yl)indol-3-yl glyoxylamide with the compounds of Formula 5, e.g., as prepared in Example 3B above, there are obtained the corresponding maleimide compounds of Formula 6.

EXAMPLE 5

5A. Formula V Where R[1] and R[2] are H and R[3] is Thianaphthen-2-yl

3-[1-(3-t-Butyldiphenylsilyloxypropyl)-2-(thianaphthen-2-yl)indol-3-yl]-1H-pyrrole-2,S-dione (49 mg), in 4 ml THF, was treated with 26 mg $Bn_4N^+F^-$ at 20° C. for 30 minutes. The mixture was applied to a preparative TLC plate and eluted with 1:1 hexane/EtOAc. The corresponding N-propanol (23 mg, 74%) was obtained as a yellow oil. It was dissolved in 4 ml $CH_2Cl_2$ and treated with 52 mg $Ph_3P$ followed by 34 mg NBS. After 15 min., the mixture was purified by preparative TLC as above (3:1 hexane/EtOAc) giving 3-[1-(3-bromopropyl)-2-(thianaphthen-2-yl)indol-3-yl]-1H-pyrrole-2,5-dione (20 mg, 86%). PMR ($CDCl_3$) 7.9–7.2 (m, 9H), 6.32 (d, J=1.3 Hz, 1H), 4.42 (t, 2H), 3.32 (t, 3H), 2.30 (m, 2H).

5B. Formula 7, Varying R[1] and R[3]

By following the procedure of Part A and substituting 3-[1-(3-t-butyldiphenylsilyloxypropyl)-2-(thianaphthen-2-yl)indol-3-yl]-1H-pyrrole-2,5-dione with the compounds of Formula 6 e.g., as prepared in Example 4B above, there are obtained the corresponding maleimide compounds of Formula 6.

EXAMPLE 6

6A. Formula I Where R[1] and R[2] are H, R[3] is Thianaphthen-2-yl and R[4] is Thiourea A mixture of 20 mg 3-[1-(3-bromopropyl)-2-(thianaphthen-2-yl)indol-3-yl]-1H-pyrrole-2,5-dione, 4 mg thiourea, and 2 ml EtOH was heated at 80° C. for 16–20 h in a sealed flask. Most of the solvent was removed in vacuo. The product was taken up in a small volume of 10% MeOH/$CH_2Cl_2$ and applied to a preparative TLC plate. After elution with 10% MeOH/$CH_2Cl_2$, the major low-running yellow band was removed and extracted with the same solvent. After concentration and refiltration (to remove traces of silica gel), the material was triturated with 3 ml of anhydrous $Et_2O$ and vigorously scratched to reduce it to a yellow-orange powder. In this way 17 mg (71%) of 3-[1-(3-isothioureidopropyl)-2-(thianaphthen-2-yl)indol-3-yl]-1H-pyrrole-2,5-dione was obtained=m.p. 170°-175° C.; PMR ($d_6$-DMSO) 8.20–7.95 (m, 2H), 7.85–7.68 (m, 3H), 7.48 (m, 2H), 7.36 (t, 1H), 7.24 (t, 1H), 6.53 (s, 1H), 4.41 (t, 2H), 3.04 (t, 2H), 2.08 (m, 2H).

6B. Formula I Where $R^2$ is H and $R^4$ Thiourea, Varying $R^1$ and $R^3$

By following the procedure of Part A and substituting 3-[1-(3-bromopropyl)-2-(thianaphthen-2-yl)indol-3-yl]-1H-pyrrole-2,5-dione with the compounds of Formula 7, e.g., as prepared in Example 5B above, there are obtained the corresponding compounds of Formula I identified in the following table:

Formula IA

| $R^1$ | $R^3$ | m.p. |
|---|---|---|
| H | Phenyl | 180° C. |
| H | 4-Methylphenyl | |
| H | Biphenyl-4-yl | 150–153° C. |
| H | Naphthalen-1-yl | 180–184° C. |
| H | Naphthalen-2-yl | 180–185° C. |
| H | 6-Methoxy-naphthalen-2-yl | 170–173° C. |
| H | 5,7-Dihydroxy-naphth-1-yl | |
| H | 5,5,8,8-tetramethyl-5,5,8,8-tetrahydro-naphthalen-2-yl | 150–155° C. |
| H | Phenanthren-2-yl | 225–228° C. |
| H | Phenanthren-3-yl | 125–130° C. |
| H | 9H-Fluoren-2-yl | |
| H | Thien-3-yl | |
| H | Thieno[2,3-b]-pyridin-2-yl | |
| H | 2,3-Dihydro-benzo[1,4]dioxin-6-yl | 130–133° C. |
| H | 2-Cyanoindol-3-yl | |
| H | Naphtho[2,1-b]-thiophen-2-yl | |
| H | Naphtho[1,2-b]-thiophen-2-yl | |
| H | Benzofuran-2-yl | 145–151° C. |
| 5-Fluoro | Benzo[b]-thiophen-2-yl | |
| 5-Chloro | Benzo[b]-thiophen-2-yl | |
| 4-Methyl | Biphenyl-4-yl | |
| 6-t-Butyl | Naphthalen-2-yl | |
| 7-Hydroxy | Phenanthren-2-yl | |
| 6-Trifluoromethyl | Thieno[2,3-b]-pyridin-2-yl | |
| 7-Nitro | Naphtho[2,1-b]-thiophen-2-yl | |
| 5-Amino | Benzofuran-2-yl | |
| 6-Dimethylamino | Benzo[b]-thiophen-2-yl | |

EXAMPLE 7

7A. Formula 8 Where $R^1$ is H and $R^3$ is Thianaphthen-2-yl

A solution of 500 mg 1-(3-t-butyldiphenylsilyloxypropyl)-2-(thianaphthen-2-yl)indole in 3 ml THF was treated with 200 mg 3-chloro-4-cyanomaleimide and stirred 30 min. at 20° C. The red solution was partitioned between EtOAc and aqueous NaHCO$_3$. The organic layer was dried over K$_2$CO$_3$ and evaporated. Purification of the residue by preparative TLC (3:1 hexane/EtOAc) afforded 400 mg of 3-[1-(3-t-butyldiphenylsilyloxypropyl)-2-(thianaphthen-2-yl)indol-3-yl]-4-cyano-1H-pyrrole-2,5-dione as a dark red glass.

7B. Formula I Where $R^1$ is H, $R^2$ is Cyano, $R^3$ is Thianaphthen-2-yl and $R^4$ is Thiourea By following the procedures of Examples 5A and 6A, substituting 3-[1-(3-t-butyldiphenylsilyloxypropyl)-2-(thianaphthen-2-yl)indol-3-yl]-1H-pyrrole-2,5-dione with 3-[1-(3-t-butyldiphenylsilyloxypropyl)-2-(thianaphthen-2-yl)indol-3-yl]-4-cyano-1H-pyrrole-2,5-dione, there is obtained 3-[1-(3-isothioureidopropyl)-2-(thianaphthen-2-yl)indol-3-yl]-4-cyano-1H-pyrrole-2,5-dione.

7C. Formula I Where $R^2$ is Cyano and $R^4$ is Thiourea, Varying $R^1$ and $R^3$ By following the procedures of Parts A and B above, substituting 1-(3-t-butyldiphenylsilyloxypropyl)-2-(thianaphthen-2-yl)indole with compounds of Formula 4 prepared, e.g., as described in Example 2B above, there are obtained the corresponding compounds of Formula I where $R^2$ is cyano and $R^4$ is thiourea, such as those identified in the following table:

Formula IB

| $R^1$ | $R^3$ | m.p. |
|---|---|---|
| H | Phenyl | |
| H | 4-Methylphenyl | |
| H | Biphenyl-4-yl | |
| H | Naphthalen-1-yl | |
| H | Naphthalen-2-yl | 257–259° C. |
| H | 6-Methoxy-naphthalen-2-yl | |
| H | 5,7-Dihydroxy-naphth-1-yl | |
| H | 5,5,8,8-tetramethyl-5,5,8,8-tetrahydro-naphthalen-2-yl | 153–158° C. |
| H | Phenanthren-2-yl | |
| H | Phenanthren-3-yl | |
| H | 9H-Fluoren-2-yl | 220–225° C. |
| H | Thien-3-yl | |
| H | Thieno[2,3-b]-pyridin-2-yl | |
| H | 2,3-Dihydro-benzo[1,4]dioxin-6-yl | |
| H | 2-Cyanoindol-3-yl | |
| H | Benzo[4,5-d]-thiazol-2-yl | |
| H | Naphtho[2,1-b]-thiophen-2-yl | |
| H | Naphtho[1,2-b]-thiophen-2-yl | |
| H | Benzofuran-2-yl | 235–240° C. |
| 5-Fluoro | Benzo[b]-thiophen-2-yl | 140–142° C. |

-continued

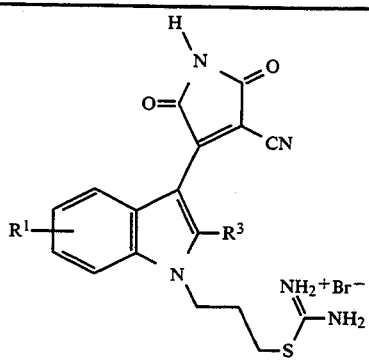

Formula IB

| R¹ | R³ | m.p. |
|---|---|---|
| 5-Chloro | Benzo[b]-thiophen-2-yl | >280° C. |
| 4-Methyl | Biphenyl-4-yl | |
| 6-t-Butyl | Naphthalen-2-yl | |
| 7-Hydroxy | Phenanthren-2-yl | |
| 6-Trifluoromethyl | Thieno[2,3-b]-pyridin-2-yl | |
| 7-Nitro | Naphtho[2,1-b]-thiophen-2-yl | |
| 5-Amino | Benzofuran-2-yl | |
| 6-Dimethylamino | Benzo[b]-thiophen-2-yl | |

EXAMPLE 8

8A. Formula 10 Where $R^1$ is H and $R^3$ is Thianaphthen-2-yl 2-(Thianaphthen-2-yl)indole (3.5 g, 14 mmol), acrylonitrile (1.49 g, 28 mmol), powdered NaOH (0.67 g, 16.8 mmol), and cetyltrimethylammonium bromide (0.15 g, 0.4 mmol) were combined in 50 mL of toluene and stirred vigorously for 2 h. TLC analysis (25% EtOAc/hexane) showed complete conversion to a lower-running compound. The cloudy reaction mixture was diluted with 70 mL of EtOAc and filtered through celite. Concentration gave 2-(thianaphthen-2-yl)indol-1-yl nitrile in high yield. No further purification was necessary.

8B. Formula 11 Where $R^1$ is H and $R^3$ is Thianaphthen-2-yl

The crude 2-(thianaphthen-2-yl)indol-1-yl nitrile from Part A above was dissolved in 30 mL of THF and a solution of BH₃·THF (1M, 21 mmol) was added. The resulting clear solution was heated to reflux for 3 h, cooled, and quenched with 10 mL of 50% THF/H₂O followed by 60 mL of 1M HCl. After 1 h, the mixture was extracted with EtOAc (3×70 mL). The organic layer was washed with brine, dried over MgSO₄ and concentrated. Chromatography over 30 g of SiO₂ using 25% EtOAc/hexane followed by 20% MeOH/CH₂Cl₂ gave 3.3 g (77%) of 1-(3-aminopropyl)-2-(thianaphthen-2-yl)indole as a yellow oil.

A suspension of 1-(3-aminopropyl)-2-(thianaphthen-2-yl)indole (3.3 g, 10.8 mmol) in 60 mL of CH₂Cl₂ treated with 1.3 mL of pyridine followed by dropwise addition of (CF₃CO)₂O (1.68 mL, 11.9 mmol). The reaction became clear following the (CF₃CO)₂O addition. After 30 min, the reaction was diluted with 150 mL of EtOAc and washed with 100 mL of sat NaHCO₃, 100 mL of brine, and dried over MgSO₄. Concentration gave 4.24 g (97%) of 1-(3-trifluoromethylacetamidopropyl)-2-(thianaphthen-2-yl)indole as a yellow crystalline solid. ¹H NMR (CDCl₃, 300 MHz) δ7.9–7.1 m (9 H), 6.79 s (1 H), 5.95 s, br (1 H), 4.9 m (2 H), 3.18 m (2 H), 2.03 m (2 H).

8C. Formula I Where $R^1$ is H, $R^2$ is CN, $R^3$ is thianaphthen-2-yl and $R^4$ is NH₂

A solution of 1-(3-trifluoromethylacetamidopropyl)-2-(thianaphthen-2-yl)indole (2.0 g, 5 mmol) in 50 mL of THF was treated with chlorocyanomaleimide at room temperature. TLC (50% EtOAc/hexane) showed the formation of a lower-running red compound ($R_f$=0.6). After 3 h, the THF was evaporated and the residue was taken up in 50 mL of hot MeOH. Filtration gave a red solution and a purple powder. The filtrate was concentrated and the residue was treated as above, only using less MeOH, two more times. The final residue was purified by SiO₂ prep. TLC (50% EtOAc/hexane) and combined with the purple powder isolated above to give 2.29 g (87%) of 3-[1-(3-trifluoromethylacetamidopropyl)-2-(thianaphthen-2-yl)indol-3-yl]-4-cyano-1H-pyrrole-2,5-dione. Elem. cacld.; C: 59.76, H: 3.28, N: 10.72. Found; C: 59.72, H: 3.25, N 10.45.

A solution of 3-[1-(3-trifluoromethylacetamidopropyl)-2-(thianaphthen-2-yl)indol-3-yl]-4-cyano-1H-pyrrole-2,5-dione (0.42 g, 0.8 mmol) in 16 mL of 1:1 THF/MeOH was treated with 5 mL of 1M NaOH and stirred at rt for 3.5 h. The reaction was diluted with 100 mL of EtOAc and washed with 75 mL of H₂O. The organic layer was washed with brine, dried over MgSO₄, and concentrated to give 0.3 g (96%) of 3-[1-(3-aminopropyl)-2-(thianaphthen-2-yl)indol-3-yl]-4-cyano-1H-pyrrole-2,5-dione as a red powder. ¹H NMR (CDCl₃, 300 MHz) δ7.85–7.35 m (9 H), 4.47 m (2 H), 2.69 m (2 H), 1.95 m (2 H). Elem. cacld. for C₂₄H₁₈N₄O₄O₂S.3 H₂O; C: 59.99, H: 5.03, N: 11.65. Found; C: 60.10, H: 4.50, N 11.15.

8D. Formula I Varying $R^1$ and $R^3$

By following the procedures of Parts A, B and C above, substituting 2-(thianaphthen-2-yl)indole with compounds of Formula 3 prepared, e.g., as described in Example 1B above, there are obtained the corresponding compounds of Formula I where $R^2$ is cyano and $R^4$ is NH₂.

EXAMPLE 9

9A. Formula 12 Where $R^1$ is H and $R^3$ is Thianaphthen-2-yl 1-(3-Trifluoromethylacetamidopropyl)-2-(thianaphthen-2-yl)indole (250 mg, 0.62 mmol) was dissolved in 6 mL of CH₂Cl₂, cooled to 0° C. and then treated, dropwise, with oxalyl chloride (0.22 mL, 2.48 mmol). The dark reaction solution was stirred for 45 min at 0° C. and transferred, via cannula, to an ice cold solution of concentrated NH₄OH (4 mL). The resulting mixture was stirred for 20 min at room temperature and then filtered through celite. The layers were separated and the aqueous layer was extracted with CH₂Cl₂ (2×20 mL). The combined organic extracts were washed with brine, dried over MgSO₄ and concentrated to give 180 mg (61%) of 1-(3-trifluoromethylacetamidopropyl)-2-(thianaphthen-2-yl)indol-3-yl glyoxylamide as a dark solid that was used in the next step without further purification.

9B. Formula IC Where $R^1$ is H and $R^3$ is Thianaphthen-2-yl

A solution of 1-(3-trifluoromethylacetamidopropyl)-2-(thianaphthen-2-yl)indol-3-yl glyoxylamide in 7 mL of 1:1 THF/MeOH was treated with 1.5 mL of 1M NaOH. The solution was stirred at room temperature for 18 h and then concentrated. The residue was taken up in CH$_2$Cl$_2$, washed with brine and dried over MgSO$_4$. Concentration gave 130 mg (90%) of 1-(3-aminopropyl)-2-(thianahthen-2-yl)indol-3-yl glyoxylamide which was used in the next step without further purification.

A suspension of KH (82 mg, 2.04 mmol) in 3 mL of DMF was treated with trimethyl phosphonoacetate (0.33 mL, 2.04 mmol) and stirred for 30 min at room temperature. The resulting phosphonate anion solution was added to a solution of 1-(3-amino-propyl)-2-(thianaphthen-2-yl)indol-3-yl glyoxylamide in 2 mL of DMF. After stirring at room temperature for 4 h, the reaction was poured into 50 mL of H$_2$O and extracted with EtOAc (4×25 mL). The organic extracts were combined, washed with brine and dried over MgSO$_4$. The higher Rf, bright yellow product was isolated by prep. TLC (10% MeOH/CH$_2$Cl$_2$). Trituration with Et$_2$O gave 75 mg (55%) of 3-[1-(3-aminopropyl)-2-(thianaphthen-2-yl)indol-3-yl]-1H-pyrrole-2,5-dione as a yellow powder. $^1$H NMR (CDCl$_3$, 300 MHz) δ7.9–7.8 m (3 H), 7.5–7.2 m (10 H), 6.24 s (1 H), 4.3 m (2 H), 2.65 m (2 H), 1.95 m (2 H). HRMS cacld. for C$_{23}$H$_{19}$N$_3$O$_2$S: 401.119799. Found: 401.119423.

9C. Formula I Varying R$^1$ and R$^3$

By following the procedures of Parts A and B, substituting 1-(3-trifluoromethylacetamidopropyl)-2-(thianaphthen-2-yl)indole with other compounds of Formula 11 prepared, e.g., as described in Examples 8A and 8B above by substituting 2-(thianaphthen-2-yl)indole with other compounds of Formula 3, e.g., prepared as described in Example 1B above, there are obtained the corresponding compounds of Formula IC where R$^2$ is H and R$^4$ is amino.

EXAMPLE 10

10A. Formula 13 Where R is Methyl, R$^1$ is H and R$^3$ is Thianaphthen-2-yl

A solution of 1-(3-trifluoromethylacetamidopropyl)-2-(thianaphthen-2-yl)indole (2.1 g, 5.22 mmol) in 17 mL of THF, maintained at 0° C. in an ice bath, was treated with KH (251 mg, 6.26 mmol) and stirred for 5 min. A catalytic amount of 18-crown-6 (8.3 mg, 0.6 mol %) was added and after 5 min, MeI (0.46 mL, 7.31 mmol) was added. The ice bath was removed and the reaction was stirred for 3 h at room temperature. The solvent was evaporated and the residue was taken up in EtOAc (20 mL) and washed with 40 mL of H$_2$O. The aqueous layer was extracted with EtOAc (2×20 mL) and the combined organic fractions were washed with brine, dried over MgSO$_4$ and concentrated to give 2.13 g (98%) of 1-[3-(N-methyltrifluoromethylacetamidopropyl)]-2-(thianaphthen-2-yl)indole as a yellow oil that was used in the next step without further purification.

10B. Formula 14 Where R is Methyl, R$^1$ is H and R$^3$ is Thianaphthen-2-yl

The alkylated acetamide from Part A above was dissolved in 73 mL of CH$_2$Cl$_2$, cooled to −25° C. and oxalyl chloride (1.78 mL, 20.4 mmol) was added dropwise. The resulting dark solution was stirred for 1 h at −25° to −20° C. and then transferred via cannula to an ice cold solution of concentrated NH$_4$H (100 mL). The resulting mixture was stirred at room temperature for 20 min and filtered through celite. The celite was rinsed with CH$_2$Cl$_2$ and the layers were separated. The aqueous layer was extracted with CH$_2$Cl$_2$ (2×100 mL) and the combined organic extracts were washed with brine, dried over MgSO$_4$ and concentrated to give 2.3 g (92%) of crude 1-[3-(N-methyltrifluoromethylacetamidopropyl)]-2-(thianaphthen-2-yl)indol-3-yl glyoxylamide that was used directly in the next step.

10C. Formula ID Where R is Methyl, R$^1$ is H and R$^3$ is Thianaphthen-2-yl

The glyoxylamide from Part B above was dissolved in 78 mL of THF containing 23.5 mL of 1M NaOH and stirred for 18 h. The reaction solution was diluted with EtOAc (200 mL) and washed with H$_2$O (500 mL). The aqueous layer was extracted with EtOAc (3×100 mL) and the combined organic extracts were washed with brine, dried over MgSO$_4$ and concentrated. The residue was dissolved in 10% MeOH/CH$_2$Cl$_2$ and filtered to remove insoluble material. Concentration gave 1.55 g (84%) of 1-[3-(N-methylaminopropyl)]2-(thianaphthen-2-yl)indol-3-yl glyoxylamide as a dark brown solid.

A suspension of KH (1.27 g, 31.68 mmol) in 20 mL of DMF was treated with trimethyl phosphonoacetate (5.13 mL, 31.68 mmol) and stirred at rt for 30 min. This solution was then added to a solution of 1-[3-(N-methylaminopropyl)]-2-(thianaphthen-2-yl)indol-3-yl glyoxylamide in 19 mL of DMF and the resulting orange solution was stirred for 3 h at room temperature. The reaction was poured into water and extracted with EtOAc (4×70 mL). Brine was added to break up the resulting suspension. The combined organic extracts were washed with brine, dried over MgSO$_4$ and concentrated. The higher Rf, bright yellow product was isolated by prep. TLC (10% MeOH/CH$_2$Cl$_2$). Trituration with Et$_2$O gave 227 mg (14%) of 3-[1-(3-N-methylaminopropyl)-2-(thianaphthen-2-yl)indol-3-yl]-1H-pyrrole-2,5-dione as a yellow powder. $^1$H NMR (CDCl$_3$, 300 MHz) δ8.1–7.9 m (2 H), 7.8–7.65 m (3 H), 7.5–7.15 m (4 H), 6.53 s (1 H), 4.35 m (2 H), 2.5 m (3 H, CH$_2$,NH), 2.25 s (3 H), 1.85 m (2 H). HRMS cacld. for C$_{24}$H$_{21}$N$_3$O$_2$S: 415.135449. Found: 415.135210.

10D. Formula ID Varying R$^1$ and R$^3$

By following the procedures of Parts A, B and C, substituting 1-(3-trifluoromethylacetamidopropyl)-2-(thianaphthen-2-yl)indole with other compounds of Formula 11 prepared, e.g., as described in Examples 8A and 8B above by substituting 2-(thianaphthen-2-yl)indole with other compounds of Formula 3, e.g., prepared as described in Example 1B above, there are obtained the corresponding compounds of Formula ID where R is methyl.

EXAMPLE 11

11A. Formula 15 Where R$^1$is H and R$^3$ is Naphthalen-2-yl 2-(Naphthalen-2-yl)indole is treated with KH until H$_2$ evolution ceases. 1-Bromo-3-dimethylaminopropane is then added and the reaction allowed to proceed for 12 hours at 25° C. The mixture is then partitioned between Et$_2$O and H$_2$O. The product 1-(3-dimethylaminopropyl)-2-(naphthalen-2-yl)indole is purified by silica gel chromatography.

11B. Formula IE Where R$^1$ is H and R$^3$ is Naphthalen-2-yl

By following the procedure of Example 7A and substituting 1-(3-t-butyldiphenylsilyloxypropyl)-2-(thianaphthen-2-yl)indole with 1-(3-dimethylaminopropyl)-2-(naphthalen-2-yl)indole, there is obtained 3-[1-(3-N-dimethylaminopropyl)-2-(naphthalen-2-yl)indol-3-yl]-4-cyano-1H-pyrrole-2,5-dione, m.p. 231°–233° C.

EXAMPLE 12

This example illustrates the preparation of a representative pharmaceutical formulation for oral administration containing an active compound of Formula I, e.g., 3-[1-(3-N-methylaminopropyl)-2-(thianaphthen-2-yl)indol-3-yl]-1H-pyrrole-2,5-dione.

| Ingredients | Quantity per tablet, mgs. |
| --- | --- |
| Active compound | 200 |
| lactose, spray-dried | 148 |
| magnesium stearate | 2 |

The above ingredients are mixed and introduced into a hard-shell gelatin capsule.

Other compounds of Formula I, such as those prepared in accordance with Examples 1-11, can be used as the active compound in the preparation of the orally administrable formulations of this example.

EXAMPLE 13

This example illustrates the preparation of another representative pharmaceutical formulation for oral administration, containing an active compound of Formula I, e.g., 3-[1-(3-N-methylaminopropyl)-2-(thianaphthen-2-yl)indol-3-yl]-1H-pyrrole-2,5-dione.

| Ingredients | Quantity per tablet, mgs. |
| --- | --- |
| Active compound | 400 |
| cornstarch | 50 |
| lactose | 145 |
| magnesium stearate | 5 |

The above ingredients are mixed intimately and pressed into single scored tablets.

Other compounds of Formula I, such as those prepared in accordance with Examples 1-11, can be used as the active compound in the preparation of the orally administrable formulations of this example.

EXAMPLE 14

This example illustrates the preparation of a representative pharmaceutical formulation containing an active compound of Formula I, e.g., 3-[1-(3-N-methylaminopropyl)-2-(thianaphthen-2-yl)indol-3-yl]-1H-pyrrole-2,5-dione.

An suspension for oral administration is prepared having the following composition:

| Ingredients | Amount |
| --- | --- |
| Active compound | 1.0 g |
| fumaric acid | 0.5 g |
| sodium chloride | 2.0 g |
| methyl paraben | 0.1 g |
| granulated sugar | 25.5 g |
| sorbitol (70% solution) | 12.85 g |
| Veegum K (Vanderbilt Co.) | 1.0 g |
| flavoring | 0.035 ml |
| colorings | 0.5 mg |
| distilled water | q.s. to 100 ml |

Other compounds of Formula I, such as those prepared in accordance with Examples 1-11, can be used as the active compound in the preparation of the orally administrable formulations of this example.

EXAMPLE 15

This example illustrates the preparation of a representative pharmaceutical formulation containing an active compound of Formula I, e.g., 3-[1-(3-N-methylaminopropyl)-2-(thianaphthen-2-yl)indol-3-yl]-1H-pyrrole-2,5-dione.

An injectable preparation buffered to a pH of 7.4 is prepared having the following composition:

| Ingredients | Amount |
| --- | --- |
| Active compound | 0.2 g |
| Sodium Acetate Buffer Solution (0.4 M) | 2.0 ml |
| HCl (1N) | q.s. to pH 7.4 |
| water (distilled, sterile) | q.s. to 20 ml |

Other compounds of Formula I, such as those prepared in accordance with Examples 1-11, can be used as the active compound in the preparation of the injectable formulations of this example.

EXAMPLE 16

This example illustrates the preparation of a representative pharmaceutical formulation containing an active compound of Formula I, e.g., 3-[1-(3-N-methylaminopropyl)-2-(thianaphthen-2-yl)indol-3-yl]-1H-pyrrole-2,5-dione.

A suppository totalling 2.5 grams is prepared having the following composition:

| Ingredients | |
| --- | --- |
| Active compound | 500 mg |
| witepsol H-15* | balance |

(*triglycerides of saturated vegetable fatty acid; a product of Riches-Nelson, Inc., New York, N.Y.).

Other compounds of Formula I, such as those prepared in accordance with Examples 1-11, can be used as the active compound in the preparation of the suppository formulations of this example.

EXAMPLE 17

In Vitro Determination of Activity Utilizing Protein Kinass C Inhibition Assay Protein Kinase C (PKC) inhibitory activity is quantitated by measuring incorporation of $^{32}P$ from $\gamma$-$^{32}P$ ATP into synthetic peptide substrates. The inhibitory potential is measured using the $\beta1$ isozyme of PKC from rat brain and the synthetic peptide substrate ala-lys-arg-arg-arg-leu-ser-ser-leu-arg-ala.

A reaction mixture containing 25 mM Tris-HCl, pH 7.5, 2.5 mM Mg(NO$_3$), 1.0 mM EGTA, 20 $\mu$M substrate, 1 $\mu$g/mL phosphatidylserine (PS), $5\times10^{-6}$M diacylglycerol(di-C8), and 50 $\mu$M ATP is spiked with $\gamma$-$^{32}P$ ATP (>5,000 Ci/mmol) to provide approximately $10^6$ CPM per reaction and 0.08 $\mu$g/mL PKC in a 50 $\mu$l volume per well. The assay is run with or without test compound, added at various concentrations. After five minutes incubation at room temperature, the reaction is stopped by the addition of 0.2V of a 50% TCA solution. A 30 $\mu$l sample from each well (control and test compound) is then spotted onto Whatman P-81 ion exchange chromatography paper, and 32-P incorporation is then counted on a Beckman LS 5000 TA liquid scintillation counter. The percent inhibition of PKC activated by $5\times10^4$M diC8 and 1 $\mu$g/mL phosphatydil serine is determined according to the formula:

% Inhibition = 1.0−[(sample CPM−basal CPM)/(total CPM−basal CPM)]×100 and the concentration necessary to achieve 50% Inhibition is determined.

The compounds of the present invention are active inhibitors of protein kinase C when tested by this method; representative compounds were determined to have the following inhibitory activities:

3-[1-(3-isothioureidopropyl)-2.-(thianaphthen-2-yl)indol-3-yl]-1H-pyrrole-2,5-dione-IC$_{50}$ 3 nM; and 3-[1-(3-aminopropyl)-2-(thianaphthen-2-yl)indol-3-yl]-1H-pyrrole-2,5-dione-IC$_{50}$ 40 nM.

EXAMPLE 18

In Vivo Determination of Activity Utilizing Small Cell Lung Carcinoma Xenograft Assay This procedure is a modification of a procedure described by Maneckjee, et al., in *Proc. Natl. Acad. Sci. USA*, Vol 89, 1169–1173 (February 1992).

H82 small cell lung carcinoma (SCLC) cells are thawed from frozen stock and grown in RPMI. Prior to injection, the cells are trypsinized, counted, and resuspended in PBS:solubilized basement membrane preparation (Matrigel ®) (1:2) to concentrations of $5 \times 10^5$ or $1.5 \times 10^6$ cells/ml. Female athymic nude mice, 4–5 weeks old (Harlan Sprague Dawley) receive 200R/mouse irradiation one day prior to challenge, and are given 0.2 ml SCLC/mouse by subcutaneous injection in the flank (concentrations of $1 \times 10^5$ or $3 \times 10^5$ SCLC cells/mouse). Groups of 30 mice are treated intraperitoneally, once a day, with test compound at 10 mg/kg (solubilized in DMSO and diluted to final vehicle concentration of 20% DMSO in PBS). Treatments are started 2 hours post-challenge and continue for 45 days. Vehicle treated and untreated mice are used as controls.

Statistical Analysis: A Fisher Exact test [Kendall M., Stuart A., *The Advanced Theory of Statistics*, Vol., 2 (MacMillan Pub. Co. N.Y., 1979)] is used to compare tumor occurrence rates between groups. The Mann Whitney U test [Hollander N., Wolfe D. A., *Non-parametric Statistical Methods* (John Wiley and Sons, Inc., N.Y., 1973)] is used to compare differences in survival time and a log rank test (Kalbfleisch J. D., Prentice R. L., *The Statistical Analysis of Failure Time Data* (John Wiley and Sons, Inc., N.Y. 1980)] is used to compare the time for each tumor to reach 2000 mm$^3$.

Compounds of the present invention inhibit tumor growth when tested by this method.

The compound 3-[1-(3-isothioureidopropyl)-2-(thianaphthen-2-yl)indol-3-yl]-1H-pyrrole-2,5-dione, when tested by this method, while not preventing SCLC tumor formation entirely, did significantly slow tumor growth. The compound (chronic LD$_{50}$ about 20 mg/kg after 6 days) exhibitied toxicity at 10 mg/kg, although no animals died. Mice treated with the compound had tumors approximately 2-fold smaller (challenge of $3 \times 10^5$ SCLC cells/mouse) or 3-fold smaller (challenge of $1 \times 10^5$ SCLC cells/mouse) than those seen for either the vehicle-treated or untreated control groups. With the challenge of $3 \times 10^5$ SCLC cells/mouse, the median time for the tumor volume to reach 2000 mm$^3$ was extended 8 days, to Day 39, as compared to Day 31 for the vehicle-treated control (p<0.001). With the challenge of $1 \times 10^5$ SCLC cells/mouse, the median time for the tumor volume to reach 2000 mm$^3$ was extended >7 days, to Day >42, as compared to Day 35 for the vehicle-treated control (p<0.001). The number of mice having tumors $\geq$2000 mm$^3$ at Day 42 of treatment was reduced with either challenge level (p<0.05).

EXAMPLE 19

In Vivo Determination of Activity Utilizing Colon Carcinoma Xenograft Assay

By following the procedure of Example 18 and substituting H82 small cell lung carcinoma cells with HT-29 colon cancer cells, grown to a concentration of $5 \times 10^6$ cells/ml and administered at a concentration of $1 \times 10^6$ cells/mouse, activity against colon carcinoma is determined.

Compounds of the present invention inhibit tumor growth when tested by this method.

The compound 3-[1-(3-isothioureidopropyl)-2-(thianaphthen-2-yl)indol-3-yl]-1H-pyrrole-2,5-dione, when tested by this method, while not preventing HT-29 tumor formation entirely, did significantly slow tumor growth. Mice treated with the compound had tumors approximately 1.5-fold smaller than those seen for either the vehicle-treated or untreated control groups. The median time for the tumor volume to reach 2000 mm$^3$ was extended 4 days, to Day 37, as compared to Day 33 for the vehicle-treated control (p<0.01). The number of mice having tumors $\geq$2000 mm$^3$ at Day 42 of treatment was reduced (p<0.05).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. All patents and publications cited above are hereby incorporated by reference.

What is claimed is:

1. A compound represented by the formula:

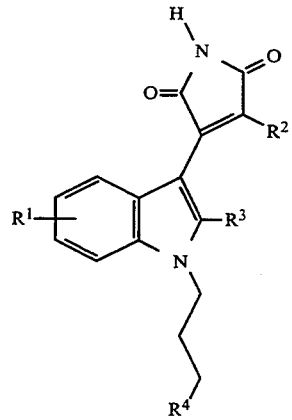

wherein:

$R^1$ is H, halo, alkyl, OH, alkoxy, haloalkyl, NO$_2$, or NR$^5$R$^6$;

$R^2$ is H or CN;

$R^3$ is aryl or heteroaryl, provided that $R^3$ is heteroaryl when $R^2$ is H and $R^4$ is $NR^5R^6$; and $R^4$ is $NR^5R^6$ or isothiourea, where $R^5$ and $R^6$ are independently H or lower alkyl;

or a pharmaceutically acceptable salt thereof.

2. The compound or salt of claim 1 wherein $R^1$ is H.

3. The compound or salt of claim 2 wherein $R^2$ is H.

4. The compound or salt of claim 3 wherein $R^4$ is $NH_2$, $NHCH_3$ or isothiourea.

5. The compound or salt of claim 4 wherein $R^3$ is thianaphthen-2-yl.

6. The compound or salt of claim 5 wherein $R^4$ is isothiourea.

7. The compound or salt of claim 5 wherein $R^4$ is $NH_2$.

8. The compound or salt of claim 1 wherein $R^2$ is H.

9. The compound or salt of claim 3 wherein $R^4$ is $NH_2$, $NHCH_3$ or isothiourea.

10. The compound or salt of claim 1 wherein $R^3$ is selected from the groups thianaphthen-2-yl, benzofuran-2-yl, naphtho[1,2-b]-thiophen-2-yl, naphtho[2,1-b]-thiophen-2-yl, 2,3-dihydro-benzo[1,4]dioxin-6-yl, thieno[2,3-b]-pyridin-2-yl, 9H-fluoren-2-yl, phenanthren-3-yl, phenanthren-2-yl, 5,5,8,8-tetramethyl-5,5,8,8-tetrahydro-naphthalen-2-yl, 6-methoxynaphthalen-2-yl, naphthalen-2-yl, naphthalen-1-yl, biphenyl-4-yl, and phenyl.

11. A method of treatment for a malignant disorder selected from tumors corresponding to H82 small cell lung carcinoma, HT-29 cancer, MCF7, MDA-MB-435 and MDA-N breast cancer, and PKC overexpressing tumors comprising administering to a mammal in need thereof a therapeutically effective amount of a compound or salt of claim 1.

12. A pharmaceutical composition comprising a compound or salt of claim 1 and a pharmaceutically acceptable excipient.

* * * * *

UNITED STATES PATENT AND TRADEMARK OFFICE
CERTIFICATE OF CORRECTION

PATENT NO. : 5,405,864

DATED : April 11, 1995

INVENTOR(S) : Chris A. Broka

It is certified that error appears in the above-identified patent and that said Letters Patent is hereby corrected as shown below:

Claim 9, at column 29, line 17 "claim 3" should read --claim 1--

Claim 10, at column 30, line 2 "the groups thianaphthen-2-yl," should read --the groups: thianaphthen-2-yl,--

Claim 11, at column 30, line 12 "HT-29 cancer," should read --HT-29 colon cancer,--

Signed and Sealed this

Twenty-seventh Day of June, 1995

Attest:

BRUCE LEHMAN

Attesting Officer     Commissioner of Patents and Trademarks